United States Patent [19]

Fleming, Jr. et al.

[11] 4,357,330

[45] Nov. 2, 1982

[54] PHARMACEUTICAL COMPOSITIONS

[75] Inventors: James S. Fleming, Jr., Manlius; Joseph P. Buyniski, Syracuse, both of N.Y.

[73] Assignee: Bristol-Myers Company, New York, N.Y.

[21] Appl. No.: 288,639

[22] Filed: Jul. 30, 1981

[51] Int. Cl.$^3$ ........................................... A61K 31/625
[52] U.S. Cl. .................................................... 424/232
[58] Field of Search ......................................... 424/232

[56] References Cited

U.S. PATENT DOCUMENTS 4,080,447  3/1978  Amselem ............................ 424/230

FOREIGN PATENT DOCUMENTS 2390957  5/1978  France .

OTHER PUBLICATIONS

*Thrombosis Res.* 15:373–388 (1979).
*J. Lab. Clin. Med.* 95 (2): 241–257 (1980).
A. Scriatabine et al., *Platelets & Thrombosis,* Baltimore University Park Press, 1974, pp. 247–262.
*British J. Eng. Path.,* 58:474–477 (1977).

*Primary Examiner*—Stanley J. Friedman
*Attorney, Agent, or Firm*—David M. Morse

[57] ABSTRACT

Supra-additive blood platelet antiaggregation activity is observed with anagrelide in combination with those non-steroidal anti-inflammatory agents which are inhibitors of platelet cyclooxygenase. The supra-additive effects of such combinations make possible new compositions and methods for both therapeutic and prophylactic treatment of thrombosis and other disorders associated with blood platelet aggregation.

5 Claims, 6 Drawing Figures

ISOBOLOGRAPHIC ANALYSIS OF THE INTERACTION BETWEEN ANAGRELIDE AND SULFINPYRAZONE VS COLLAGEN-INDUCED AGGREGATION IN VITRO

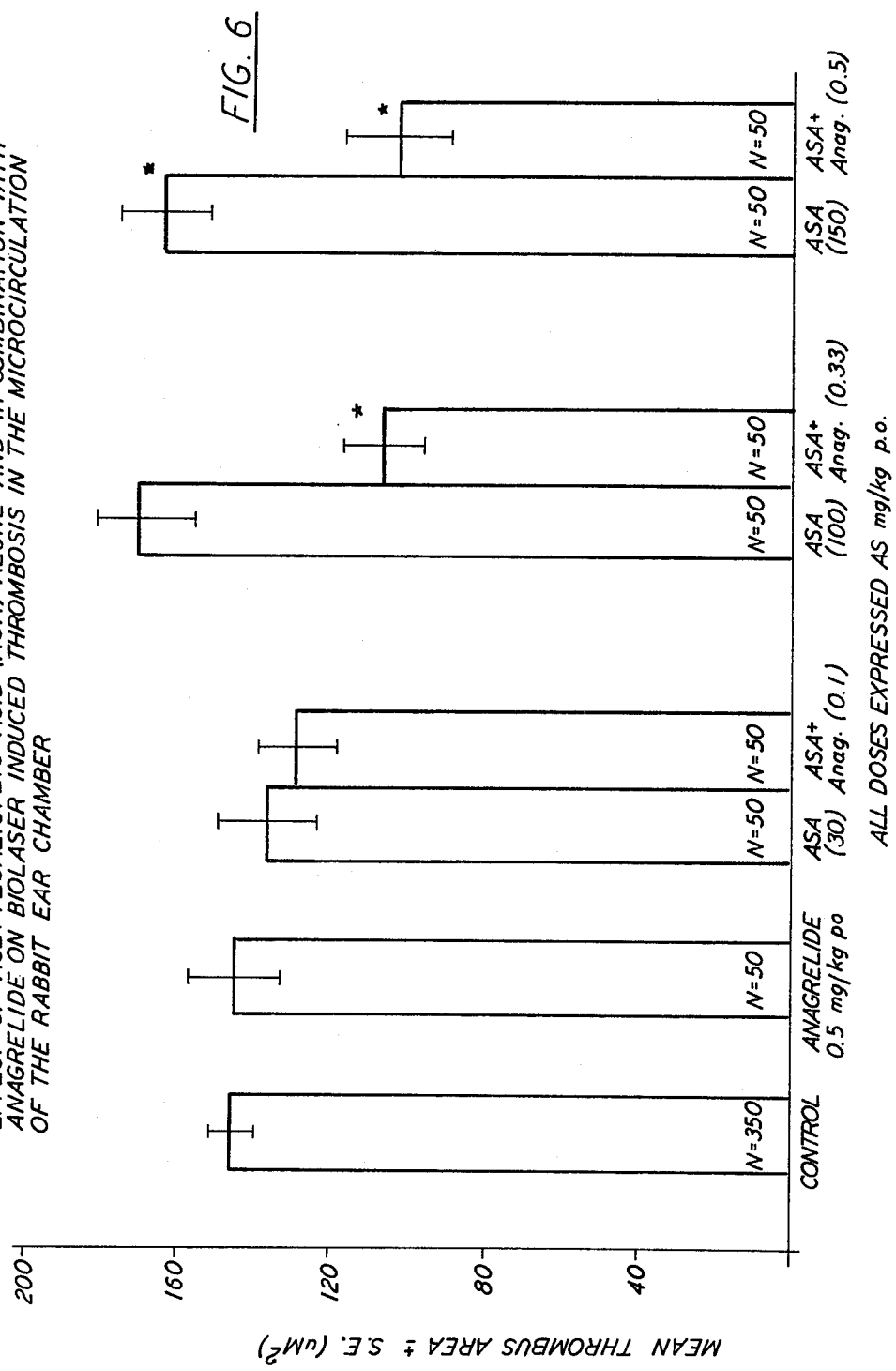

PHARMACEUTICAL COMPOSITIONS

BACKGROUND OF THE INVENTION

1. Field of the Invention

This invention is directed toward improved methods and compositions for inhibiting blood platelet aggregation.

2. Description of the Prior Art

A number of non-steroidal anti-inflammatory agents such as acetylsalicylic acid (aspirin), zomepirac, ibuprofen, naproxen, sulfinpyrazone, phenylbutazone and indomethacin have been found to be inhibitors of blood platelet aggregation. The presumed mechanism of action of such agents is inhibition of the blood platelet cyclooxygenase enzyme which ultimately leads to inhibition of collagen-induced platelet aggregation. Aspirin and sulfinpyrazone have been evaluated clinically for the prevention of stroke and heart attack and aspirin has been approved for prevention of transient cerebral ischemic attacks and stroke.

Anagrelide having the chemical name 6,7-dichloro-1,5-dihydroimidazo[2,1-b]quinazolin-2(3H)-one and the structural formula

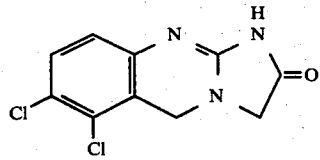

has been recently reported to be a potent inhibitor of platelet aggregation induced by a variety of aggregating agents. This potent activity has been observed in vitro in platelet rich plasma, ex vivo following oral dosing in animals and in several in vivo animal models following oral administration. Anagrelide has also been shown to inhibit aggregation when administered orally to man (Circulation 62: III-277, 1980). Anagrelide appears to be uniquely different from the non-steroidal anti-inflammatory agents in that it produces a broad spectrum effect, i.e. it blocks not only collagen-induced release and aggregation and the second wave of ADP (adenosine diphosphate)-induced aggregation but also the first phase of ADP-induced aggregation as well as aggregation induced by thrombin, arachidonic acid and antigen-antibody complex (Thrombosis Research 15: 373–388, 1979). Recent studies indicate that anagrelide acts in part by selective inhibition of blood platelet low $K_m$ cyclic AMP (adenosine monophosphate) phosphodiesterase (J. Lab. Clin. Med. 95(2): 241–257, 1980).

Certain blood platelet antiaggregation agents have been found to exhibit a supra-additive interaction when combined. Representative of such supra-additive combinations are the following:

1. Platelets and Thrombosis, A. Scriabine and S. Sherry (Eds.), Baltimore, University Park Press, 1974, pg. 247–262 at p. 256 discloses that a combination of acetylsalicyclic acid and prostaglandin $E_1$ exhibited supra-additive interaction against both collagen-and ADP-induced platelet aggregation.

2. Fed. proc. 38(3): 419 (1979) reports that supra-additive interaction is exhibited between combinations of anagrelide and prostaglandin $I_2$ and combinations of anagrelide and prostaglandin $I_2$-S (the 6,9-thia analog of prostaglandin $I_2$) with respect to ADP-or collagen-induced aggregation.

3. Br. J. Exp. Path. 58: 474–477 (1977) discloses an in vivo supra-additive effect between acetylsalicylic acid and the antithrombotic agent SH 1117 with respect to ADP-induced aggregation.

4. J. Lab. Clin. Med. 95(2): 241–257 (1980) discloses that anagrelide potentiates the inhibitory effect of prostaglandin $E_1$ on platelet function and the prostaglandin $E_1$-induced elevation of cylic 3′,5′-adenosine monophosphate (c AMP) basic level.

5. U.S. Pat. No. 4,080,447 discloses the supra-additive interaction of acetylsalicylic acid and ticlopidine with respect to blood platelet antiaggregation activity.

6. U.S. Pat. No. 4,206,214 discloses that a combination of dipyridamole and sulfinpyrazone exhibits a supra-additive antithrombotic effect.

7. French Pat. No. 2,390,959 (Farmdoc 14511B/08) discloses inter alia the supra-additive antiaggregation activity of acetylsalicylic acid and dipyridamole.

8. Acta Univ. Carol. Med. Monogr. 72: 199–210 discloses in vitro supra-additive interaction with certain combinations of five drugs, i.e. metergoline, dipyridamole, acetylsalicylic acid, nimergoline and 5-adenosylmethionine.

SUMMARY OF THE INVENTION

It has now been found according to the present invention that supra-additive blood platelet antiaggregation activity is observed with anagrelide in combination with those non-steroidal anti-inflammatory agents which are inhibitors of platelet cyclooxygenase. The supra-additive effects of such combinations demonstrated by both in vitro and in vivo tests make possible new compositions and methods for both therapeutic and prophylactic treatment of thrombosis and other disorders associated with blood platelet aggregation.

BRIEF DESCRIPTION OF THE DRAWINGS

FIG. 6 shows the supra-additive interaction of anagrelide and acetylsalicylic acid on biolasar-induced thrombosis in the microcirculation of the rabbit ear chamber.

DETAILED DESCRIPTION OF THE INVENTION

Figure 1:
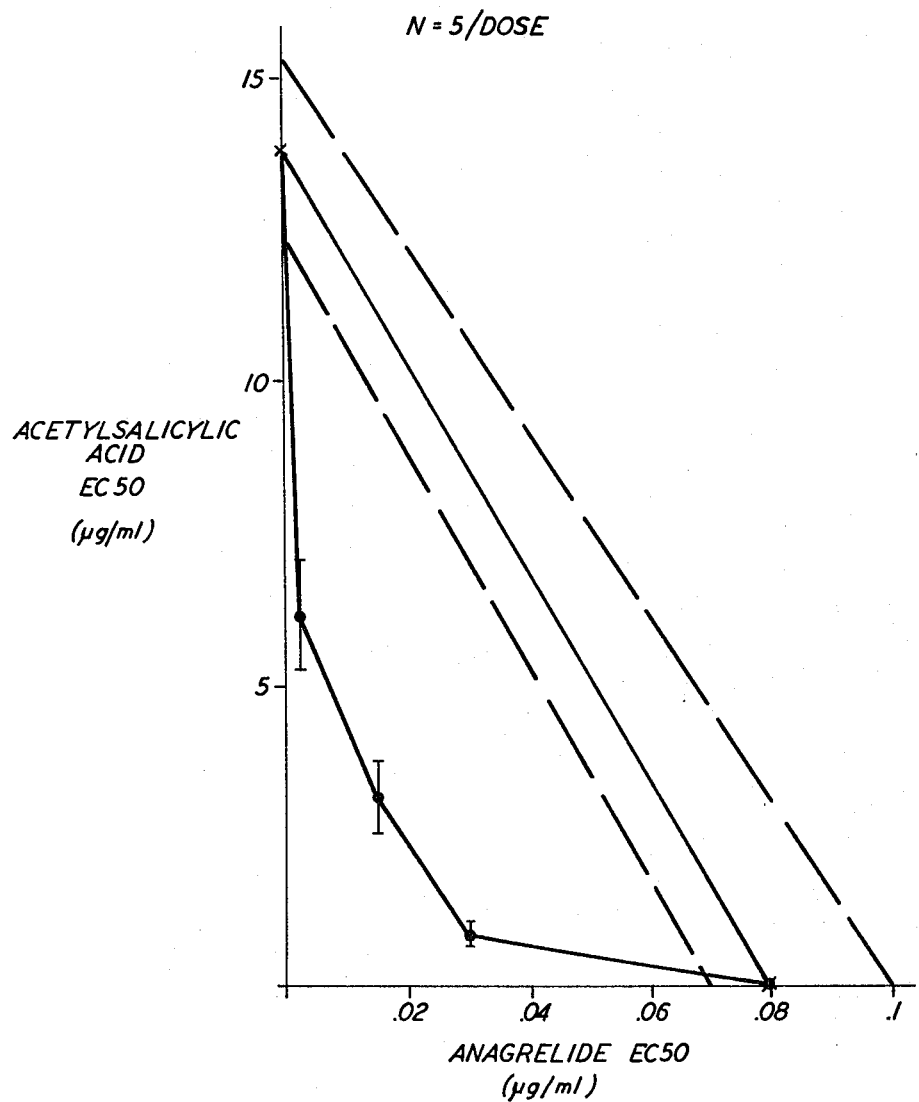
FIG. 1 is an isobolographic analysis showing the supra-additive platelet antiaggregation activities of several mixtures of anagrelide and acetylsalicylic acid.

In one aspect the present invention relates to a method for inhibiting blood platelet aggregation which comprises orally administering to a mammal in need of such treatment, either simultaneously or sequentially, anagrelide and a non-steroidal anti-inflammatory agent capable of inhibiting blood platelet cyclooxygenase.

In another aspect the present invention relates to oral pharmaceutical compositions comprising, as active ingredient, anagrelide and a non-steroidal anti-inflammatory agent capable of inhibiting blood platelet cyclooxygenase, said compositions providing an enhanced (supra-additive) inhibitory activity on blood platelet aggregation.

We have surprisingly discovered that when anagrelide and a non-steroidal anti-inflammatory agent capable of inhibiting blood platelet cyclooxygenase are administered together to a mammal, most preferably a human patient, a strong supra-additive inhibitory activity on blood platelet aggregation is produced, whereby the antiaggregation effects of the combination are greater than the sum of the effects produced by each component acting alone. This unexpected supra-additive interaction makes possible extremely potent antiaggregative activity for prophylactic and therapeutic treatment of thrombosis and other disorders associated with platelet aggregation. Alternatively, the supra-additive effect allows the dosage of anagrelide which would normally be required for achievement of a certain level of antiaggregation activity to be substantially reduced, thus reducing side-effects which may be produced with high doses of this drug.

The supra-additive effect of anagrelide and non-steroidal anti-inflammatory cyclooxygenase inhibitors has been demonstrated in vitro against collagen-induced platelet aggregation in rabbit platelet rich plasma by the optical density method of Born (J. Physiol. 162: 67 P, 1962) as modified by Mustard, et al. (J. Lab. CLin. Med. 64: 548, 1964). In addition, the combination of anagrelide and acetylsalicylic acid was evaluated in vivo in the rabbit ear chamber biolasar model of intravascular thrombosis (Platelets and Thrombosis, A. Scriabine and S. Sherry (Eds.), Baltimore, University Park Press, 1974, p.247).

Although, for convenience, the simple term "anagrelide" is usually used herein and in the claims, it is specifically intended that this invention include the use of nontoxic pharmaceutically acceptable acid addition salts of anagrelide and the term anagrelide, therefore, encompasses all of such salts as well as the parent compound. Suitable salts of anagrelide are disclosed in U.S. Pat. No. 3,932,407 and include the hydrochloride, hydrobromide, hydroiodide, (lower)alkylsulfates, (lower)alkyl-and arylsulfonates, phosphate, sulfate, maleate, fumarate, succinate, tartrate and citrate. Anagrelide hydrochloride is a particularly preferred acid addition salt.

Similarly, although the simple terms "acetylsalicylic acid," "zomepirac," "ibuprofen," "naproxen," "sulfinpyrazone," "phenylbutazone" and "indomethacin" are used herein and in the claims to refer to certain preferred non-steroidal anti-inflammatory cyclooxygenase inhibitors, it is specifically intended that this invention include the use of nontoxic pharmaceutically acceptable salts of such agents. All of the above-named agents may form salts with pharmaceutically acceptable bases and such salts are, unless otherwise indicated, encompassed by the generic name of the parent compound. Sulfinpyrazone is the generic name for 1,2-diphenyl-4-(2-phenylsulfinylethyl)pyrazolidone-3,5-dione which is described along with its salts in U.S. Pat. No. 2,700,671. Indomethacin is the generic name for 1-(4-chlorobenzoyl)-5-methoxy-2-methyl-1H-indole-3-acetic acid which is described in U.S. Pat. No. 3,161,654. Naproxen is the generic name for d-2-(6-methoxy-2-naphthyl)propionic acid which along with its salts (including the sodium salt which is preferred) is described in U.S. Pat. No. 3,904,682. Phenylbutazone is the generic name for 4-butyl-1,2-diphenyl-3,5-pyrazolidinedione which is disclosed in U.S. Pat. No. 2,562,830. Ibuprofen is the generic name for 2-(4-isobutylphenyl)-propionic acid which is disclosed in U.S. Pat. No. 3,385,886. Zomepirac is the generic name for 5-(p-chlorobenzoyl)-1,4-dimethylpyrrole-2-acetic acid which along with its salts (including the sodium salt which is preferred) is disclosed in U.S. Pat. No. 3,752,826.

In practicing the present invention, the anagrelide and non-steroidal anti-inflammatory agent are preferably administered orally. In prepared solid oral dosage forms, any of the usual pharmaceutical granulating agents, lubricants, binders, disintegrating agents, starches, sugars or the like may be used to prepare such dosage forms as tablets, capsules or powders. For liquid oral preparations, one may utilize water, glycols, oils, alcohols or the like, along with coloring agents, preservatives, flavors or the like, to prepare solutions, elixers, syrups, suspensions, etc.

The weight ratio of the non-steroidal anti-inflammatory agent to anagrelide which results in supra-additive interaction may vary within wide limits. The precise ratios to be employed for a particular combination may be readily ascertained using a conventional in vitro aggregometry method (optical density) such as described below. For the preferred combinations, the ratios of anti-inflammatory agent to one part by weight of anagrelide are as follows:

(a) Ibuprofen
   67–3524 parts by weight, preferably 150–2400 parts by weight
(b) Naproxen
   261–831 parts by weight, preferably 275 to 750 parts by weight
(c) Acetylsalicylic acid
   30–2468 parts by weight, preferably 150–2400 parts by weight
(d) Zomepirac
   22–178 parts by weight, preferably 25–175 parts by weight
(e) Sulfinpyrazone
   262–3013 parts by weight, preferably 400–3000 parts by weight The preferred single doses for humans of the preferred non-steroidal anti-inflammatory agents and anagrelide are as follows:
Anagrelide: 0.025–1.0 mg, preferably 0.1–0.5 mg, most preferably 0.25 mg
Acetylsalicylic acid: 150–600 mg,
Ibuprofen: 150–600 mg,
Sulfinpyrazone: 100–400 mg,
Naproxen: 125–375 mg,
Zomepirac: 50–200 mg. Preferred doses of other suitable anti-inflammatory components may be readily ascertained from the literature, i.e. the normal doses used for anti-inflammatory purposes. The particular dosage of anagrelide and the anti-inflammatory component to be administered will of course vary depending on such factors as the host being treated (i.e. animal species, age, weight, general health), severity of the symptoms, the particular disease being treated, kind (if any) of concurrent treatment with other drugs, frequency of treatment, etc. Such dosages will be preferably administered up to twice a day and most preferably once a day.

To provide a supra-additive combination, doses of the non-steroidal anti-inflammatory agent and anagrelide are selected so that (1) the weight ratio of the combination is within the synergistic weight ratio range indicated above and (2) the doses of the components are within the acceptable effective dosage ranges for the host being treated. For example, for human patients, the preferred dose of anagrelide is from about 0.025 mg to 1 mg, more preferably 0.1 to 0.5 mg and most preferably about 0.25 mg. The dose of acetylsalicylic acid, for example, to be combined with the anagrelide is selected so that (1) the weight ratio of acetylsalicylic acid/anagrelide is from about 30-2468 (preferably about 150-2400) parts by weight of acetylsalicylic acid per part by weight of anagrelide and (2) the dosage of acetylsalicylic acid is within the safe and effective dosage for human patients, i.e. 150-600 mg. Thus, a suitable combination might be 0.25 mg anagrelide and 150 mg acetylsalicylic acid. Similarly, suitable human doses of other preferred combinations are as follows:

Ibuprofen: 0.25 mg anagrelide, 150 mg ibuprofen.
Naproxen: 0.25 mg anagrelide, 125 mg naproxen.
Zomepirac: 0.5 mg anagrelide, 50 mg zomepirac.
Sulfinpyrazone: 0.25 mg anagrelide, 200 mg sulfinpyrazone.

Since the use of anagrelide and the non-steroidal anti-inflammatory agent in combination results in a supra-additive anti-aggregation effect, it is contemplated that the doses of anagrelide and/or the anti-inflammatory agent used may be those which by themselves are only minimally effective in inhibiting platelet aggregation.

Although the present invention contemplates that the anagrelide and anti-inflammatory components may be administered separately, it is particularly advantageous and convenient to formulate compositions of anagrelide and the anti-inflammatory agent in unitary dosage form, i.e. physically discrete units which each contain the quantity of anagrelide and anti-inflammatory agent calculated to produce the desired supra-additive effect, together with any desired pharmaceutical carrier. Such unitary forms may be in the form of capsules, pills, tablets, powder packets, wafers, teaspoonfuls, tablespoonfuls and the like.

The compositions and methods of the present invention may be used in the same manner as known blood platelet antiaggregation agents. Thus, the anagrelide and non-steroidal anti-inflammatory agent may be added to whole blood for in vitro applications such as storage of whole blood in blood banks and whole blood to be used in heart-lung machines. In vivo applications include the administration to humans and other mammals such as mice, rats, dogs, cats, horses, etc. to prevent clot formation in situations such as following surgery (to prevent postoperative thrombosis), in geriatric patients to prevent transient ischemic attacks and in long term prophylaxis following myocardial infarcts and strokes.

Tests for Assessing Platelet Antiaggregation Activity

A. In vitro test

The drugs used in this study were anagrelide hydrochloride, zomepirac sodium, naproxen, acetylsalicylic acid, ibuprofen and sulfinpyrazone.

The study of the platelet aggregation inhibitory activities of anagrelide/zomepirac, anagrelide/naproxen, anagrelide/acetylsalicylic acid, anagrelide/ibuprofen and anagrelide/sulfinpyrazone combinations, as well as the individual drugs, was carried out using the standard optical density aggregometry procedure of Born (J. Physiol. 162: 67P-68P, 1962) as modified by Mustard, et al. (J. Lab. Clin. Med. 64: 548-559, 1964) with collagen-induced platelet aggregation in rabbit platelet rich plasma.

Platelet rich plasma was prepared from rabbit blood drawn into syringes containing 3.8% sodium citrate (1 ml citrate/9 ml of blood) followed by 10 minutes of centrifugation at 920 rpm (200× g). All glassware used for preparation of platelet rich plasma was silicontreated. Collagen (0.05 ml of bovine Achilles tendon in Tyrode's solution-see Evans, et al. J. Exp. Med. 128: 877-894, 1968) was used to induce aggregation in 0.9 ml platelet rich plasma samples. The test compounds or vehicle (0.005 ml) were added using a microliter syringe to the platelet rich plasma sample three minutes before the addition of the collagen. Inhibition of platelet aggregation was assessed by comparing maximal optical density changes of drug-treated platelet rich plasma samples with vehicle-treated platelet rich plasma samples using a Payton aggregometer (Payton Assoc., Inc., Buffalo, N.Y.). Dimethylsulfoxide was used as the vehicle for in vitro testing. The platelet antiaggregation effect was measured by the determination of the $EC_{50}$'s (concentration of drug that inhibited peak induced platelet aggregation by 50%). $EC_{50}$ values were determined from computer-generated regression equations based on probit analysis and the method of Finney (Probit Analysis, pg. 50-80, 230-268, University Press, Cambridge, England, 3rd Ed., 1971). Platelet antiaggregation interaction may be observed by the isobolographic method of Loewe (*Arzneim. Forsch.* 9: 429-456, 1956) as modified by Gessner and Cabana (*J. Pharmacol. Exp. Ther.* 174: 247-259, 1969).

Various fixed concentrations of anagrelide were combined with each of the anti-inflammatory agents which were then evaluated for activity against induced platelet aggregation in a dose-response manner. $EC_{50}$ values were then determined for the combination and the component ratio for each $EC_{50}$ was calculated. Thus, using the isobolographic analysis of Loewe, it can be determined whether the observed $EC_{50}$'s were significantly different from those expected on the basis of the effects of the individual drugs, and whether this interaction represented supra-additive, infra-additive or additive action.

Figure 2:
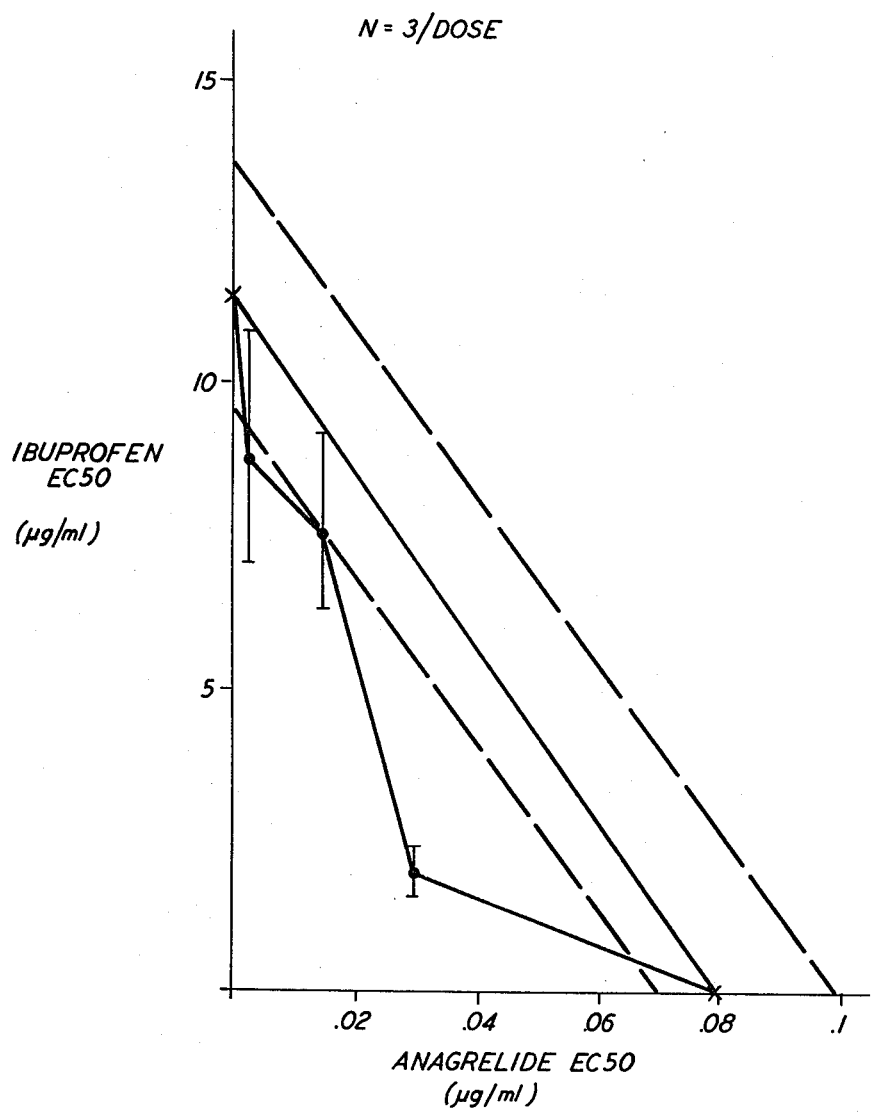
FIG. 2 is an isobolographic analysis showing the supra-additive platelet antiaggregation activities of several mixtures of anagrelide and ibuprofen.
Figure 3:
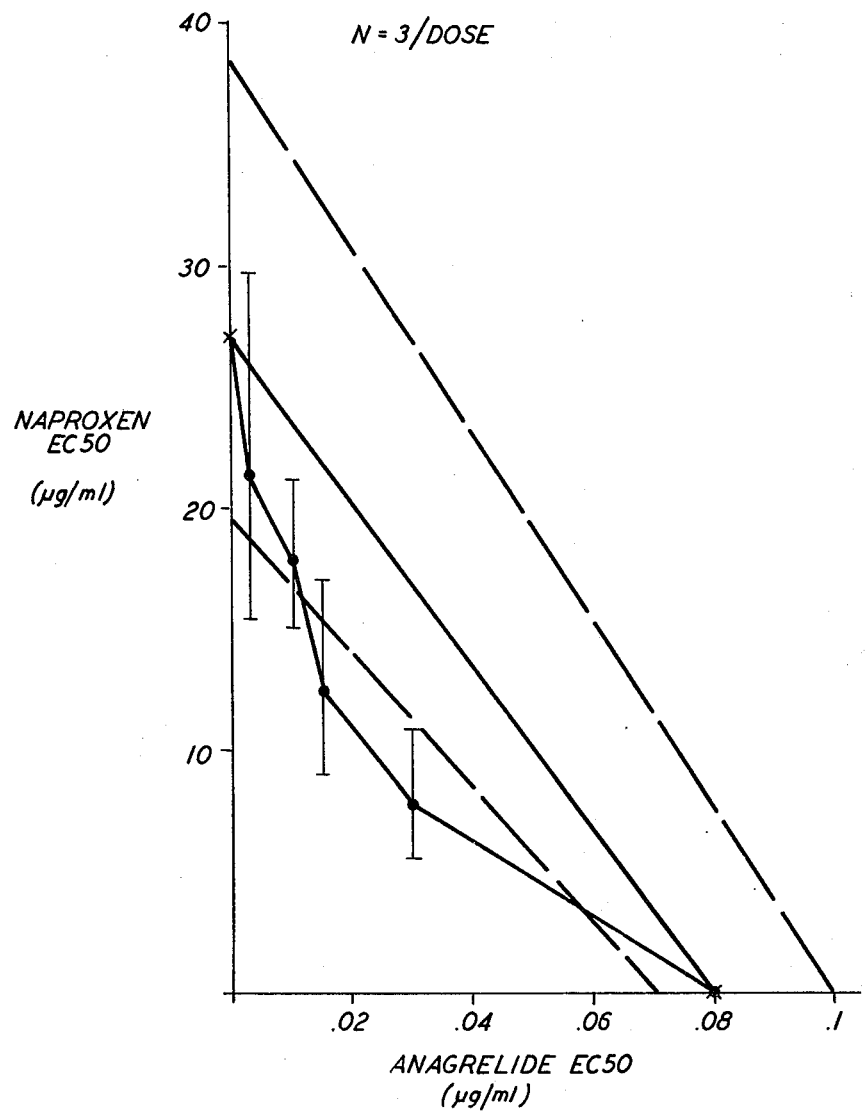
FIG. 3 is an isobolographic analysis showing the supra-additive platelet antiaggregation activities of several mixtures of anagrelide and naproxen.
Figure 4:
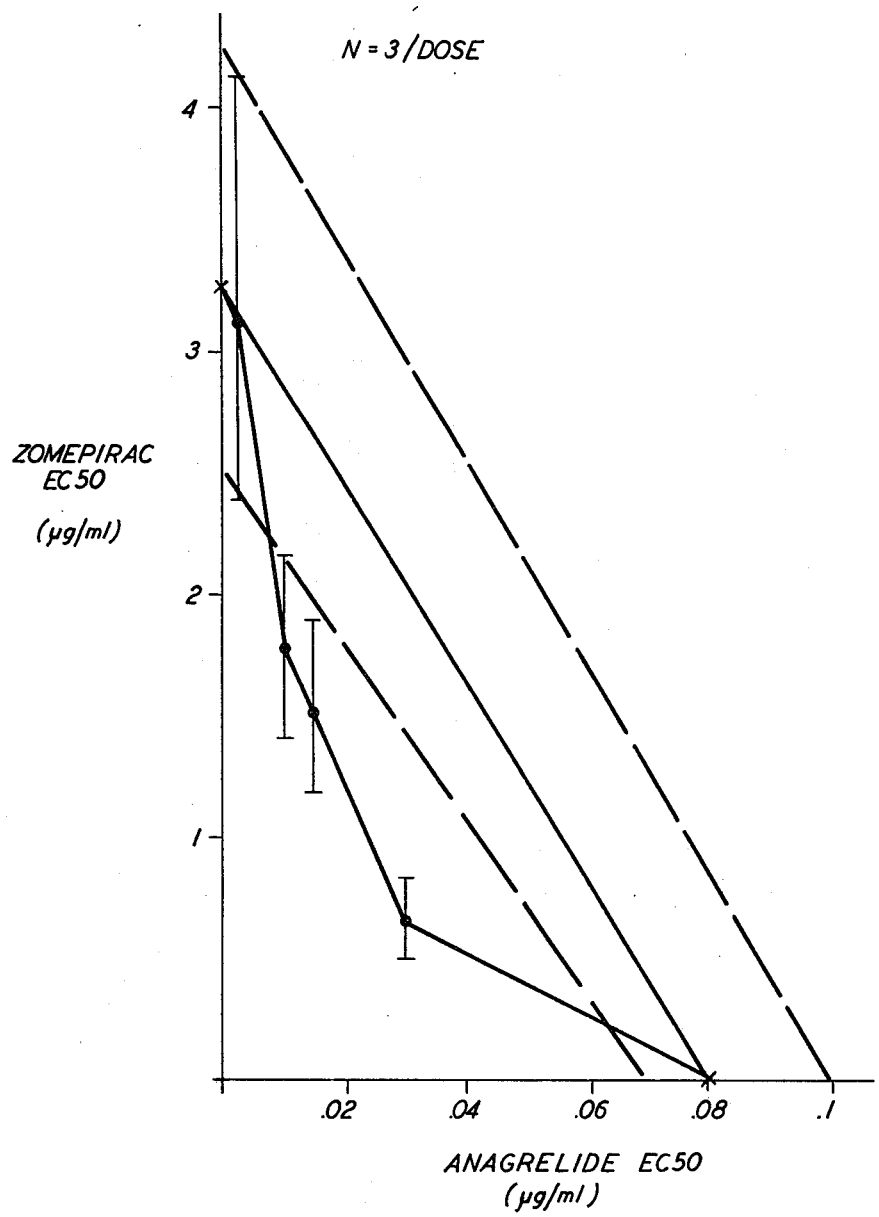
FIG. 4 is an isobolographic analysis showing the supra-additive platelet antiaggregation activities of several mixtures of anagrelide and zomepirac.
Figure 5:
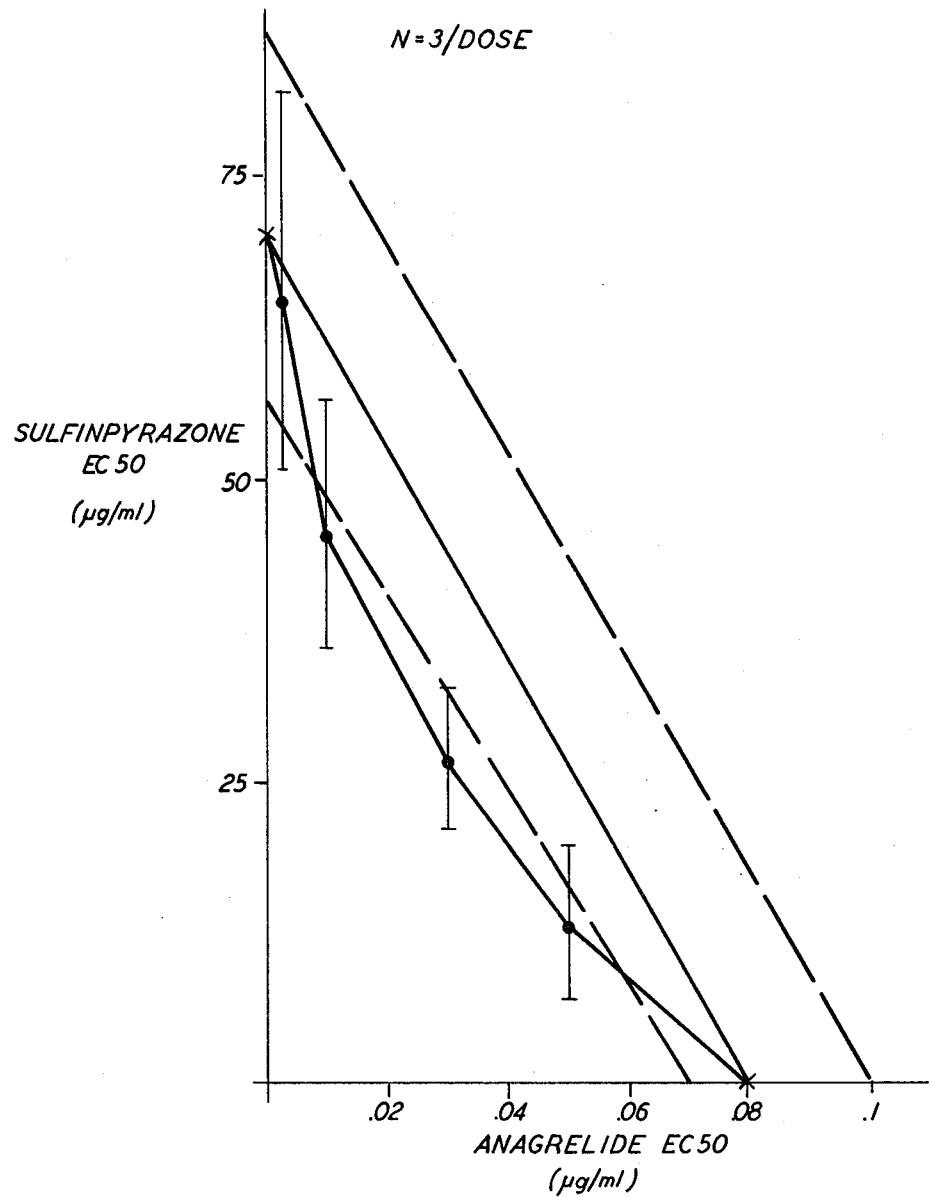
FIG. 5 is an isobolographic analysis showing the supra-additive platelet antiaggregation activities of several mixtures of anagrelide and sulfinpyrazone.

Isobolographic analyses of the in vitro effects of the various drug combinations vs collagen-induced platelet aggregation are shown in FIGS. 1-5. The $EC_{50}$ value of the non-steroidal anti-inflammatory cyclooxygenase inhibitor alone is plotted on the ordinate while the $EC_{50}$ for anagrelide alone is plotted on the abscissa. These points are then connected by a line which is the isobol line. If two compounds interact in an additive fashion, all combinations of the two which yield a 50% effect should, theoretically, fall on the isobol line. The two dashed lines on either side of the isobol line represent its 95% confidence limits. If two compounds interact in a supra-additive manner, the points should fall to the left of the isobol line. On the other hand, if the two compounds antagonize one another, the points should fall to the right of the isobol line. In the case of anagrelide and acetylsalicylic acid, marked supra-additive interaction is seen with all three combinations falling well to the left of the isobol line. The other drug combinations studied also demonstrated supra-additive interaction, although the degree of interaction was not as extensive as that observed with the anagrelide/acetylsalicylic acid combination.

A comparison of the observed and expected $EC_{50}$ values are shown in Table I below.

TABLE I

Comparison of Expected and Observed Antiaggregation $EC_{50}$ Values

| Test Agents Alone and in Combination | In vitro $EC_{50}$'s + 95% Confidence Limits (μg/ml of Variable Component) | | Weight Ratio |
|---|---|---|---|
| | Observed | Expected | |
| Anagrelide | 0.08 (0.07–0.10) | — | — |
| Acetylsalicylic acid | 13.8 (12.5–15.3) | — | — |
| Anagrelide (0.03)[1] + acetylsalicylic acid | 0.89 (0.71–1.09)* | 8.6 (7.1–10.7) | 1:30* |
| Anagrelide (0.015)[1] + acetylsalicylic acid | 3.17 (2.58–3.79)* | 11.2 (9.8–13.0) | 1:211* |
| Anagrelide (0.0025)[1] + acetylsalicylic acid | 6.17 (5.31–7.11)* | 13.3 (12.0–14.9) | 1:2468* |
| Anagrelide | 70.3 (56.5–87.3) | — | — |
| Anagrelide (0.05)[1] + sulfinpyrazone | 13.1 (7.1–20.0)* | 26.0 (16–43) | 1:262* |
| Anagrelide (0.03)[1] + sulfinpyrazone | 26.6 (21.2–33.0)* | 44 (32.5–61) | 1:887* |
| Anagrelide (0.015)[1] + sulfinpyrazone | 45.2 (36.0–56.6)* | 61.5 (48.5–78.5) | 1:3013* |
| Anagrelide (0.0025)[1] + sulfinpyrazone | 64.9 (50.8–82.1) | 68 (54.5–85) | 1:25,960 |
| Ibuprofen | 11.45 (9.61–13.66) | — | — |
| Anagrelide (0.03)[1] + ibuprofen | 2.00 (1.64–2.41)* | 7.1 (5.5–9.5) | 1:67* |
| Anagrelide (0.015)[1] + ibuprofen | 7.64 (6.30–9.25)* | 9.3 (7.65–11.60) | 1:509* |
| Anagrelide (0.0025)[1] + ibuprofen | 8.81 (7.11–10.9)* | 11.1 (9.3–13.35) | 1:3524* |
| Zomepirac | 3.26 (2.52–4.27) | — | — |
| Anagrelide (0.03)[1] + zomepirac | 0.66 (0.50–0.85)* | 2.05 (1.40–3.0) | 1.22* |
| Anagrelide (0.015)[1] + zomepirac | 1.51 (1.19–1.92)* | 2.65 (1.98–3.65) | 1.101* |
| Anagrelide (0.01)[1] + zomepirac | 1.77 (1.45–2.16)* | 2.85 (2.15–3.85) | 1:178* |
| Anagrelide (0.0025)[1] + zomepirac | 3.15 (2.39–4.17) | 3.15 (2.38–4.18) | 1:1260 |
| Naproxen | 27.1 (19.4–38.6) | — | — |
| Anagrelide (0.03)[1] + naproxen | 7.84 (5.55–10.84)* | 16.5 (11.0–26.7) | 1:261* |
| Angrelide (0.015)[1] + naproxen | 12.47 (9.02–17.06)* | 21.7 (15.2–32.6) | 1:831* |
| Anagrelide (0.01)[1] + naproxen | 17.8 (15.0–21.1) | 23.5 (16.7–34.5) | 1:1782 |
| Anagrelide (0.0025)[1] + naproxen | 21.3 (15.3–29.8) | 26.0 (19.8–37.5) | 1:8512 |

*Significant supra-additive interaction - the observed $EC_{50}$ of the combination falls below the 95% confidence limits of the expected value
[1]Fixed dose of anagrelide (μg/ml) used in combination B. In vivo test The combination of anagrelide (as the hydrochloride salt) and acetylsalicylic acid was evaluated in vivo in the rabbit ear chamber-biolaser model of intravascular thrombosis (J. Pharmacol. Exp. Ther. 194: 453, 1975).

Direct microscopic observation of drug effects on the formation and fate of induced intravascular platelet thrombi was accomplished in unanesthetized half-lop rabbits by means of chronically implanted transparent ear chambers of the type described by Sanders, et al. in Brit. J. Exp. Path. 35: 331, 1954. The chamber was modified in that it did not have the removable pin. The rabbits were conditioned to lie quietly in a supine position. A microscope (Leitz Ortholux, Ernst Leitz GmbH, Wetzlar, Germany) was used to focus a single pulse ruby laser beam (TRG model 512 Biolaser, Hadron Inc., Westbury, N.Y.) into the lumen of a vessel 10 to 30 μM in diameter. The resulting microburn evoked the formation of a small thrombus that consisted of platelets accumulated around a core of one or two damaged red cells. Thrombi areas were determined as the product of two perpendicular measurements (length and diameter) using a micrometer eyepiece. The mean thrombus area ($\mu M^2$) obtained for ten trials served as the control value. Subsequently, the test compounds were administered orally at the doses desired and two hours later a second series of laser-induced thrombi were formed. Results were compared to controls in terms of thrombus area by means of the "t" test for paired data.

It is known that acetylsalicylic acid produces a dose-related inhibition of biolaser-induced intravascular thrombosis (Thrombosis Research 15: 373, 1979). However, acetylsalicylic acid is inactive in this test model over a wide range of oral doses (30–150 mg/kg). If sub-threshold doses of anagrelide (e.g. 0.5 mg/kg po) are combined with various doses of acetylsalicylic acid, significant inhibition of experimental thromobosis is observed. The results shown in FIG. 6 indicate that when acetylsalicylic acid and anagrelide are combined in the ratio of 300:1, significant inhibition of thrombosis is observed with two different combinations, i.e. acetylsalicylic acid 100 mg/kg po + anagrelide 0.33 mg/kg po and acetylsalicylic acid 150 mg/kg po + anagrelide 0.5 mg/kg po.

We claim:

1. An oral pharmaceutical composition having an inhibitory activity on blood platelet aggregation consisting essentially of anagrelide and acetylsalicyclic acid, wherein the weight ratio of acetlysalicyclic acid to anagrelide is from about 30:1 to about 2468:1.

2. A composition according to claim 1 in unitary dosage form wherein the anagrelide is present in an amount of from about 0.025 to 1 mg and the acetylsalicylic acid is present in an amount of from about 150 to 600 mg.

3. A composition of claim 1 or claim 2 which contains in addition a pharmaceutically acceptable carrier.

4. An oral pharmaceutical composition in unitary dosage form comprising an active ingredient a combination of 0.25 mg anagrelide and 150 mg acetylsalicylic acid.

5. A method for inducing blood platelet antiaggregation activity in a mammalian host in need of such treatment which comprises orally administering to said host, simultaneously or sequentially, an effective blood platelet aggregation inhibiting amount of a combination of anagrelide and acetylsalicylic acid, wherein the weight ratio of acetylsalicylic acid to anagrelide is from about 30:1 to about 2468:1.

* * * * *